United States Patent [19]

Meitzler et al.

[11] Patent Number: 5,365,770
[45] Date of Patent: Nov. 22, 1994

[54] ULTRASONIC WAVE INTERFEROMETERS

[75] Inventors: Allen H. Meitzler, Ann Arbor; Edward N. Sickafus, Grosse Ile, both of Mich.

[73] Assignee: Ford Motor Company, Dearborn, Mich.

[21] Appl. No.: 43,957

[22] Filed: Apr. 5, 1993

[51] Int. Cl.$^5$ .................... G01P 15/08; H03H 9/30
[52] U.S. Cl. ................... 73/24.06; 73/64.53;
   73/517 AV; 73/505; 250/338.4; 250/370.14;
   310/313 R; 310/313 D; 324/244; 324/260
[58] Field of Search ........... 310/313 R, 313 B, 313 D,
   310/329; 73/517 AV, 517 R, 516 R, 24.01,
   24.06, 54.41, 64.53; 324/244, 260; 250/336.1,
   338.1, 338.4, 370.01, 370.14

[56] References Cited

U.S. PATENT DOCUMENTS

| | | | |
|---|---|---|---|
| 3,680,008 | 7/1972 | Yamamoto | 333/30 R |
| 3,810,257 | 5/1974 | Jones et al. | 310/313 B |
| 3,878,477 | 4/1975 | Dias et al. | 310/313 B |
| 3,967,221 | 6/1976 | Cooper et al. | 310/313 D |
| 4,055,072 | 10/1977 | Fletcher et al. | 73/24.01 |
| 4,130,813 | 12/1978 | Sandy et al. | 310/313 R |
| 4,209,759 | 6/1980 | Volluet | 310/313 R |
| 4,268,808 | 5/1981 | Meengailis | 333/195 |
| 4,306,456 | 12/1981 | Maerfeld | 73/517 R |
| 4,341,998 | 7/1982 | Castera et al. | 324/244 |
| 4,349,794 | 9/1982 | Kagiuada et al. | 333/141 |
| 4,361,026 | 11/1982 | Muller et al. | 73/24.01 |
| 4,447,754 | 5/1984 | Wagers | 310/313 |
| 4,467,235 | 8/1984 | De Wames et al. | 73/517 R |
| 4,594,889 | 6/1986 | McCarthy | 73/204 |
| 4,598,224 | 7/1986 | Ballato | 310/313 R |
| 4,598,587 | 7/1986 | Dwyer et al. | 73/517 R |
| 4,932,255 | 6/1990 | Brace et al. | 73/204.11 |
| 5,011,818 | 4/1991 | Katoka et al. | 324/248 |
| 5,173,667 | 12/1992 | Meitzler | 310/313 D |

FOREIGN PATENT DOCUMENTS

PCT/FR87/-
 00058 3/1987 France .

OTHER PUBLICATIONS

Martin et al, "Sensing in Liquids with SH Plate Mold Devices", 1988 Ultrasonics Symposium Proceedings, vol. 1, pp. 607–611.

-LIGA-, "Movable Microstructures", Institut für Mikro-otuktuitechnik, Karesruhe, Germany, pp. 1–12.

Nieuwenhuizen et al, "Surface Acoustic Wave Chemical Sensors", Sensors and Materials, 5 (1989), pp. 261–300.

Primary Examiner—Hezron E. Williams
Assistant Examiner—Rose M. Finley
Attorney, Agent, or Firm—Peter Abolins; Roger L. May

[57] ABSTRACT

An acoustic or ultrasonic device includes two ultrasonic energy transmission paths having substantially identical transmission characteristics for a neutral condition of the device. One or both of the transmission paths include path altering structure(s) or coating(s) for changing the transmission characteristics of one or both of the paths in response to a physical phenomenon to be sensed or monitored. The paths have input transducers coupled thereto for transmitting ultrasonic energy into the paths. The input transducers are driven by a single oscillator such that the ultrasonic energy waves generated in the two paths are substantially identical to one another. A drive adjusting circuit compensates for any differences between the two paths and/or the ultrasonic waves in the two paths. An output transducer is coupled to the two paths for receiving ultrasonic waves from the paths and generating an output signal which is the result of combining the acoustic or ultrasonic waves from the two paths. By combining the waves from the two paths, the output signal is effectively the interference pattern generated by the waves in the two paths and hence the device operates as an acoustic or ultrasonic energy interferometer to sense or monitor physical phenomena to which the path altering structure(s) or coating(s) respond.

21 Claims, 5 Drawing Sheets

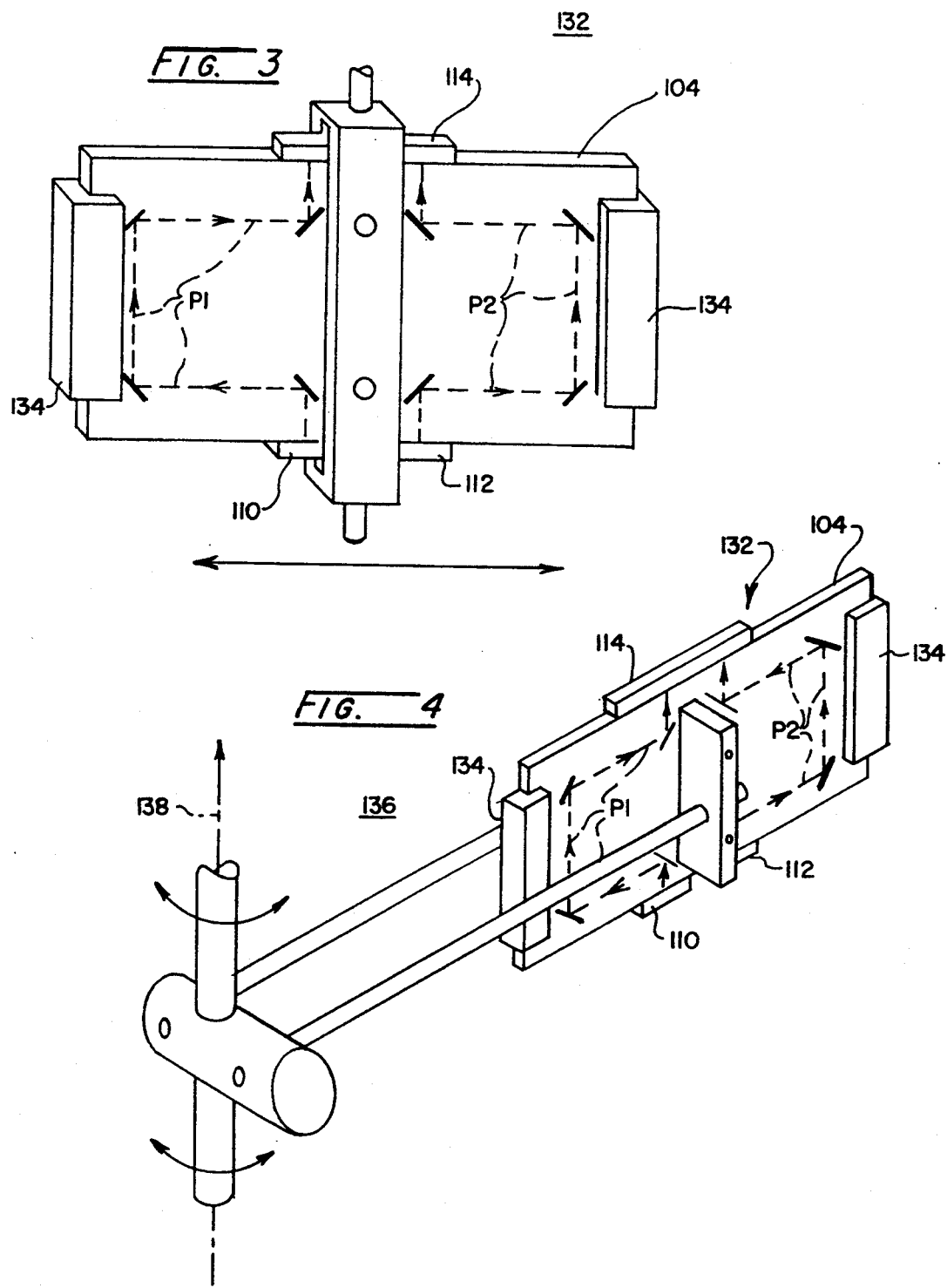

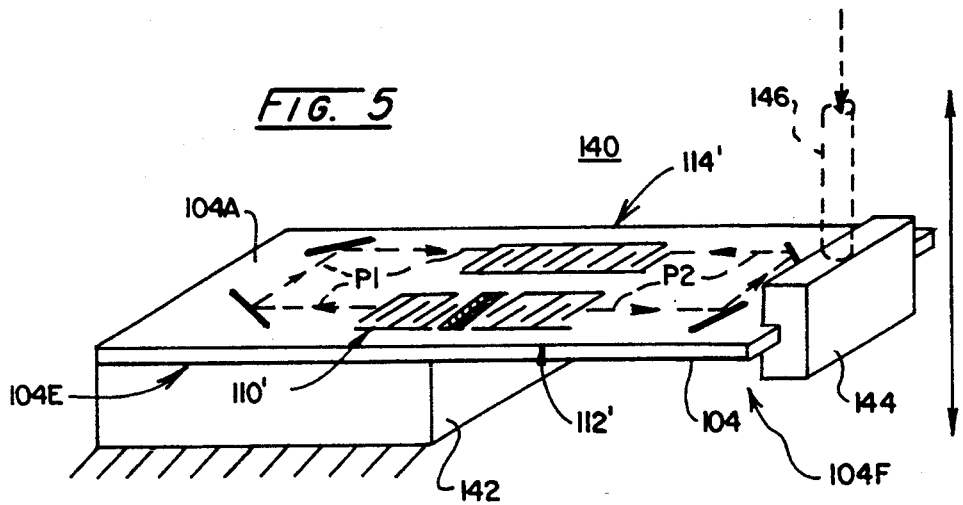
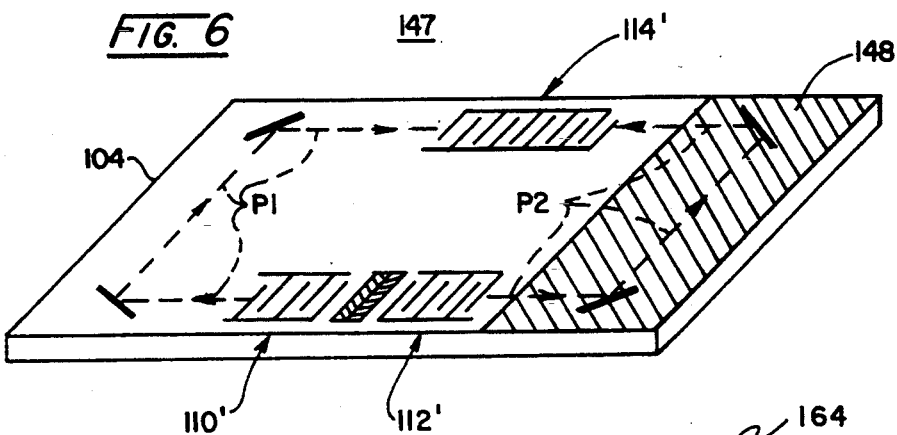
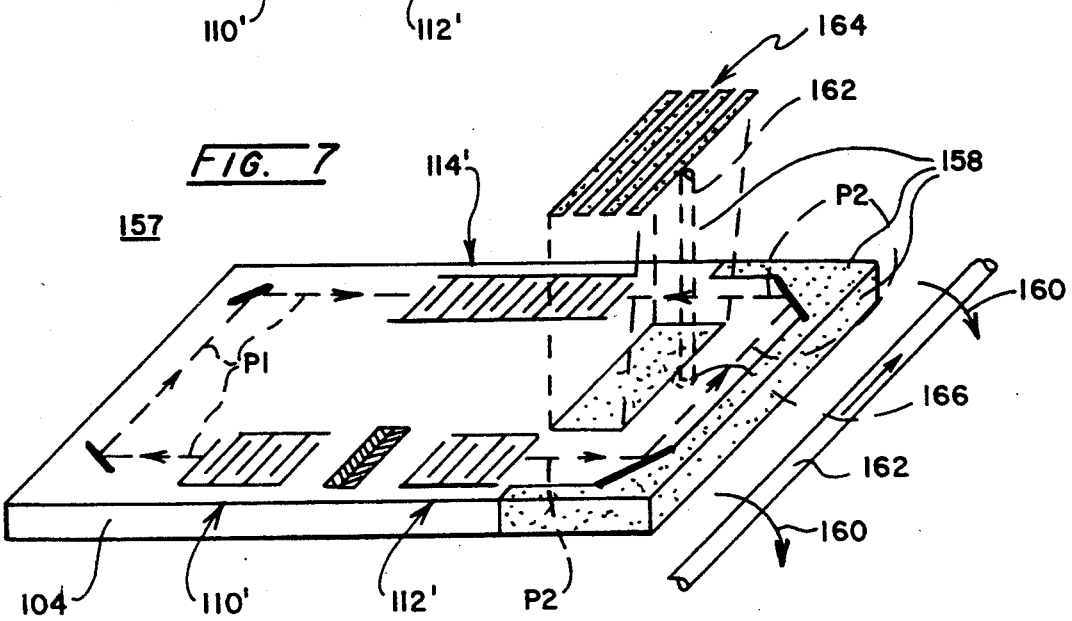

ULTRASONIC WAVE INTERFEROMETERS

BACKGROUND OF THE INVENTION

The present invention relates generally to devices for transmitting ultrasonic energy waves and, more particularly, to methods and apparatus for performing ultrasonic wave interferometry and for using ultrasonic wave interferometers for sensing physical phenomena.

As used herein, an ultrasonic wave interferometer is defined as an ultrasonic energy transmitting device including a pair of separate ultrasonic energy paths having substantially equal transmission path characteristics when the device is in a neutral condition relative to a physical phenomenon to be sensed. At least one of the paths is treated to respond to the physical phenomenon to be sensed such that its transmission path characteristics change as a result of the phenomenon to vary an interference pattern defined at the output of the device. Although the wave energy used in the present invention is ultrasonic, the term acoustic has come to be equivalent in the art and, accordingly, the two terms will be used interchangeably herein.

A wide variety of processes are controlled in response to sensing chemical concentrations, visual as well as other electromagnetic radiation, magnetic field strength, acceleration, angular velocity, applied forces, and other parameters which will be collectively referred to herein as physical phenomena. Such sensing is performed by devices which convert the physical phenomenon being sensed into electrical signals. The resulting electrical signals can then be used to control a related process or to warn or inform personnel performing a sensing or monitoring operation. It is apparent that the automation and accurate control of many processes depends on the availability of reliable sensors.

Preferably, sensors are compact, robust and inexpensive, particularly in applications where multiple sensing operations must be reliably performed in hostile environments for proper operation and control of complex operating systems. An example of such a control environment is a modern motor vehicle. Such vehicles include a variety of operating systems which must be accurately monitored and controlled for safe and effective operation of the systems and hence the vehicles.

One currently available sensor arrangement utilizes an ultrasonic energy transmission device wherein two isolated delay lines are incorporated into a pair of substantially identical oscillators. Accordingly, the device, including a substantial amount of associated circuitry, is referred to as a dual delay line oscillator circuit.

The amplitudes of oscillation of the oscillators are preferably controlled by means of automatic gain control circuits (AGC's). A physical phenomenon to be sensed, such as a gas concentration around the sensor, is monitored by coating one of the delay lines with a material (chemical or biochemical interface) which alters the transmission characteristics of the delay line in response to the phenomenon. Alteration of the transmission characteristics of the delay line in turn alters the frequency of oscillation of the oscillator circuit including the delay line. The oscillator output signals are mixed and passed through a low pass filter to generate a signal having a frequency which is representative of the phenomenon.

While the dual delay line oscillator circuit can reliably sense gas concentrations and other physical phenomena, it requires substantial circuitry in addition to the device or devices which define the acoustic or ultrasonic delay lines. There is thus a need for an improved and simplified arrangement which can be used to measure physical phenomena without requiring the amount of support circuitry required by the dual delay line oscillator circuit.

SUMMARY OF THE INVENTION

This need is met by the apparatus and methods of the present invention wherein an acoustic or ultrasonic device includes two ultrasonic energy transmission paths having substantially identical transmission characteristics for a neutral condition of the device. One or both of the transmission paths include path altering means for changing the transmission characteristics of one or both of the paths in response to a physical phenomenon to be sensed or monitored.

Each of the transmission paths has an input transducer coupled to an input end for transmitting ultrasonic energy into the path. The input transducers are driven by a single oscillator such that the ultrasonic energy waves generated in the two paths of the device are substantially identical to one another. Drive adjustment means can be included in the circuit to at least one of the paths to compensate for any differences between the two paths and/or the ultrasonic waves generated by the drive signals.

An output transducer is coupled to output ends of the two paths for receiving ultrasonic waves from the paths and generating an output signal which is the result of combining the acoustic or ultrasonic waves from the two paths. By combining the waves from the two paths, the output signal is effectively the interference pattern generated by the waves in the two paths and hence the device operates as an interferometer utilizing acoustic or ultrasonic waves.

Preferably, the neutral condition of the device corresponds to a null of the interference pattern or output signal from the output transducer. Sensor sensitivity is increased by defining a null for the neutral condition since movements from zero or null are easier to sense and quantify.

Another useful arrangement is to make one path differ from the other by one-quarter wavelength ($\frac{1}{4}\lambda$). The quarter wavelength difference between the two paths permits sensing the direction of change of the characteristics of the path which is being varied in response to a physical phenomenon being measured.

In accordance with one aspect of the present invention, an ultrasonic wave device comprises ultrasonic wave transmission media means for defining substantially isolated first and second ultrasonic wave paths therethrough. The first and second paths each have an input end and an output end and define substantially equal transmission characteristics for a neutral condition of the device. Ultrasonic wave transmitting means is coupled to the media means for introducing ultrasonic waves into the input ends of the paths and ultrasonic wave receiving means is coupled to the media means for receiving ultrasonic waves from the paths. The ultrasonic wave receiving means generates an output signal representative of the combination of the ultrasonic waves from the paths as they are received. Drive circuit means is connected to drive the ultrasonic wave transmitting means to generate ultrasonic waves in the paths, and receiver circuit means is connected to receive the output signal generated by the ultrasonic wave receiving means. Preferably, at least one of the paths comprises path altering means coupled thereto for changing the transmission characteristics of at least one of the paths as the result of a physical phenomenon such that the physical phenomenon can be sensed by alteration of the neutral condition of the device.

In accordance with another aspect of the present invention, an ultrasonic wave device for performing ultrasonic wave interferometry comprises first and second substantially isolated ultrasonic transmission paths defining substantially equal transmission characteristics when the device is in a neutral condition. A first transducer is coupled to the first path for launching ultrasonic waves therein and a second transducer is coupled to the second path for launching ultrasonic waves therein. The ultrasonic waves launched in the first and second paths are effectively identical to one another. A third transducer is coupled to the first and second paths for receiving ultrasonic waves transmitted therethrough and for generating an output signal representative of the combination of the ultrasonic waves received from the paths. Coupler means are provided for coupling a physical phenomenon to at least one of the first and second ultrasonic transmission paths such that the physical phenomenon can be detected.

In accordance with yet another aspect of the present invention, a method of sensing physical phenomena by means of ultrasonic energy comprises the steps of: defining substantially isolated first and second ultrasonic energy paths having substantially equal transmission lengths when the first and second paths are in a neutral condition; coupling a physical phenomenon to at least one of the first and second ultrasonic energy paths; passing substantially identical ultrasonic energy waves through the first and second ultrasonic energy paths; receiving and combining ultrasonic energy transmitted through the first and second ultrasonic energy paths; and, generating a signal indicative of the combination of ultrasonic energy received after transmission through the first and second ultrasonic energy paths, the signal being representative of the physical phenomenon.

It is thus a feature of the present invention to provide an improved ultrasonic wave device for sensing physical phenomena and converting the phenomena into electrical signals by forming an acoustic or ultrasonic interferometer.

Other features and advantages of the invention will be apparent from the following description, the accompanying drawings and the appended claims.

BRIEF DESCRIPTION OF THE DRAWINGS

FIGS. 3–9 illustrate, in simplified schematic views, a variety of physical phenomena sensors incorporating the acoustic or ultrasonic wave interferometers of FIGS. 1 and 2.

DETAILED DESCRIPTION OF THE INVENTION

The present invention relates to acoustic or ultrasonic wave interferometers which are illustrated herein for use as a sensing component in a variety of devices used to sense physical phenomena. This invention is an expansion of the principles of interferometry which are used extensively in optical applications to perform minute distance measurements based on the interference patterns which occur between two coherent optical beams. Optical wavelengths are very short, on the order of 0.5 micrometer, such that a path length variation of half a wavelength in an optical interferometer changes the combination of the light beam waves at the output of the interferometer from a condition of constructive or additive interference (maximum output) to a condition of destructive interference (minimum output).

The present invention applies the principles of interferometry with coherent wave motions to acoustic or ultrasonic waves in solid acoustic energy transmitting devices. These devices are then used to sense a wide variety of physical phenomena by making one path in the device responsive to a phenomenon to be sensed or measured.

The acoustic interferometers described herein preferably are relatively small, miniature devices on the order of one centimeter or less on a side. Many of the devices specifically concern acoustic waves in rectangular solid plates formed from single-crystal silicon. However, some of the devices can also be formed by using polycrystalline metal plates formed by known processing technologies that involve a combination of photolithography and electroplating. LIGA (German acronym for Lithographie, Galvanoformung, Abformiung) is one example of such a processing technology.

For the devices formed from single-crystal silicon, the plates of silicon include an arrangement of cavities with both straight walls and sloping walls formed by processes referred to herein as silicon micromachining. Silicon micromachining techniques were developed from integrated circuit processing technology and offer many of the advantages associated with integrated circuit processing. For example, the ability to make low-cost, miniature, precisely-formed components by the use of photolithography and batch fabrication. The details of forming silicon plates with the combination of straight wall and sloping wall cavities that have ultrasonic wave reflecting and absorbing characteristics, respectively, is described in U.S. Pat. No. 5,173,667 which was issued to Allen H. Meitzler on Dec. 22, 1992, is assigned to the assignee of the present application and is hereby incorporated by reference.

Figure 1:
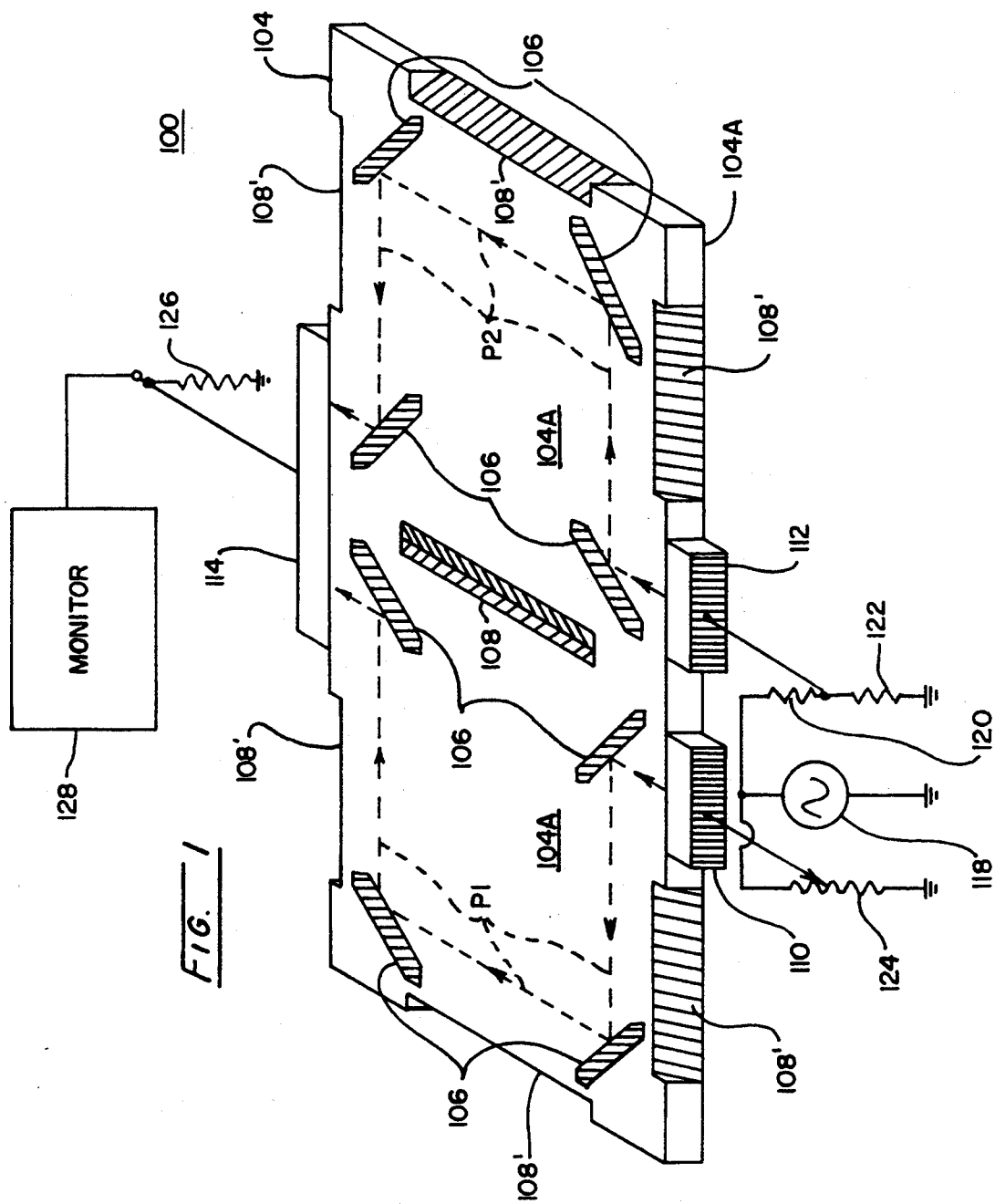
FIG. 1 is a perspective view of a first embodiment of an acoustic or ultrasonic wave interferometer in accordance with the present invention wherein shear horizontal-polarization acoustic wave (SHAW) energy is used.
Figure 2:
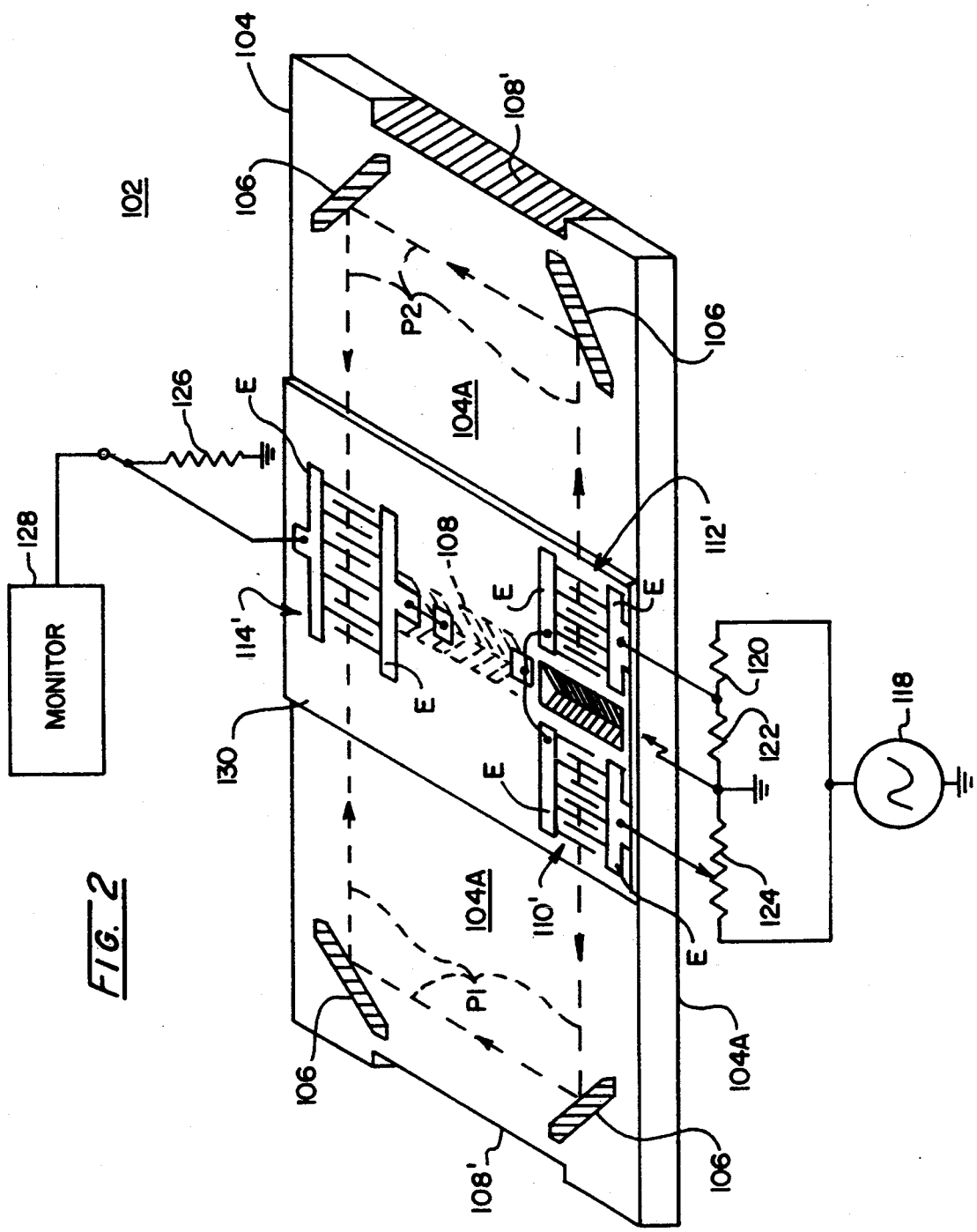
FIG. 2 is a perspective view of a second embodiment of an acoustic or ultrasonic wave interferometer in accordance with the present invention wherein surface acoustic wave (SAW) energy is used.

Two illustrative embodiments of acoustic wave interferometers 100, 102 of the present invention are shown in FIGS. 1 and 2. The two embodiments each utilize a silicon plate 104 which plates are substantially the same and include similar acoustic or ultrasonic energy wave paths P1 and P2 defined by straight wall cavities 106. The paths P1 and P2 are separated and substantially isolated from one another to prevent spurious acoustic waves from coupling from one path to the other. Isolation is performed by physical separation of the paths, by the radiation patterns due to beam forming and directional response, and also by a sloping wall cavity 108 or sloping wall recesses 108' in the sidewalls of the silicon plate 104.

The recesses 108' may be formed originally as sloping-wall cavities by a micromachining process during processing of a silicon wafer before the wafer is separated into individual devices. An acoustic absorbing material (not shown) preferably is used to coat the sloping walls of the cavity 108 and the recesses 108'. The combination of the sloping walls and the acoustic absorber serve to absorb and remove unwanted side lobes of the acoustic beams travelling in the paths P1, P2.

The two embodiments of FIGS. 1 and 2 are distinguished from one another by the types of acoustic or ultrasonic wave motion used, and hence the types of transducers and frequency ranges of operation. Due to the substantial similarities, corresponding elements will be identified by the same identifying numerals for both illustrative embodiments and also for the illustrative sensors of FIGS. 3-9.

The first embodiment, acoustic wave interferometer 100 shown in FIG. 1, uses shear horizontal-polarization acoustic wave (SHAW) transducers and is best suited for low-frequency applications (20 MHz or lower). SHAW wave motion is the lowest mode of shear wave motion that propagates in a plate with parallel major faces 104A. The particle displacements in the acoustic wave motion are perpendicular to the propagation direction for the wave and parallel to the major faces 104A of the silicon plate 104.

The SHAW transducers of FIG. 1 include ultrasonic wave transmitting means comprising: a first transducer 110 coupled to the silicon plate 104 to launch ultrasonic waves in the first path P1, a second transducer 112 coupled to the silicon plate 104 to launch ultrasonic waves in the second path P2; and, a third transducer 114 coupled to the silicon plate 104 for receiving ultrasonic waves transmitted through the paths P1, P2. The transducers 110, 112 are rectangular solids attached to the sides of the silicon plate 104 adjacent acoustic energy input ends of the paths P1, P2. The transducer 114 is a rectangular solid attached to the side of the silicon plate 104 adjacent acoustic energy output ends of the paths P1, P2.

Each of the input transducers 110, 112 is several wavelengths long in its long dimension in order to form the radiated acoustic wave motion into a beam along the paths P1, P2, respectively. The two beams are combined to achieve the interferometer effect in the output or third transducer 114. The two signal paths P1, P2 each include four 90° changes in direction at the four straight wall cavities 106 positioned along the paths P1, P2.

For the majority of applications, the most sensitive way of using the interferometers is to adjust the operation to a null condition with zero loading of the device, i.e. for a neutral condition of the device. This can be done by arranging the polarization directions of the input transducers 110, 112 to be oppositely phased, so that, if the acoustic paths have the same lengths, the wave motions cancel one another at the output transducer 114.

The input transducers 110, 112 are driven by a constant frequency oscillator 118. A pair of fixed resistors 120, 122 determine a fixed signal level for driving the second transducer 112, and a variable resistor 124 permits adjustment of the amplitude of the signal level for driving the first transducer 110. This arrangement permits amplitude adjustment for the two wave motions to attain substantially complete cancellation in the output or third transducer 114 which requires that the two wave motions added be equal in amplitude and opposite in phase. In addition, if necessary for a given application, phase adjustment can be added electrically or otherwise into one or both of the paths P1, P2.

Although the ultrasonic waves arrive at two different regions of the output or third transducer 114, they are added together by the fact that the electrodes (not shown) on the transducer 114, one secured to the side of the silicon plate 104 and one to receiver circuit means comprising an output resistor 126, effectively connect the two regions in parallel to form a resultant output signal voltage on the resistor 126. The voltage developed across the resistor 126 is supplied to an input of monitoring means comprising a signal processing circuit 128, microprocessor or the like.

The second embodiment, acoustic wave interferometer 102 shown in FIG. 2, uses surface acoustic wave (SAW) transducers and is best suited for high-frequency applications (from approximately 0.1 GHz to 1.0 GHz) and silicon plates that are 1 cm or less in their length and width. The wave motion for this embodiment is a Rayleigh surface wave motion that propagates along the upper surface of the silicon plate 104 with most of the acoustic energy of the wave motion being localized within approximately one wavelength ($\lambda$) of the surface of the silicon plate 104. The SAW motion has two displacement components, one perpendicular to the surface and one parallel to the surface and the propagation direction.

The transducers used to initiate and receive surface wave motions are interdigital transducers 110', 112' and 114' shown in FIG. 2 as having interdigitated fingers which extend from opposed electrodes E. Here again there are two input transducers or first and second transducers 110', 112' and one output transducer or the third transducer 114'. The transducer fingers are several wavelengths, ten (10) or more, long in order to form well-defined beams of radiated energy directed along the paths P1, P2 shown in FIG. 2. The straight wall cavities 106, sloping wall cavity 108 and sloping wall recesses 108' perform the same functions as described above relative to the SHAW embodiment or acoustic wave interferometer 100. The surface wave transducers require a film 130 of piezoelectric material to convert the electric fields between the transducer fingers to mechanical motions and vice-versa. Sputtered films of zinc-oxide are widely used to perform this function. In some applications it may be desirable to have the zinc-oxide film cover the entire upper surface of the sensor to reduce reflections from discontinuities.

The input transducers 110' and 112' are driven by a constant frequency oscillator 118. Here again, a pair of fixed resistors 120, 122 determine a fixed signal level for driving the second input transducer 112', and a variable resistor 124 permits adjustment of the amplitude of the signal level for driving the first input transducer 110'. This arrangement permits amplitude adjustment for the two wave motions to attain substantially complete cancellation in the output or third transducer 114' which requires that the two wave motions added be equal in amplitude and opposite in phase. In addition, if necessary for a given application, phase adjustment can be added electrically or otherwise into one or both of the paths P1, P2.

A distinctive difference between the SHAW and SAW devices is that the surface wave transducers 110', 112', 114' permit the two wave motions to be combined in the same spatial region since the surface wave transducers are ordinarily bidirectional. The output transducer 114' sums the responses of the two incident wave motions received from the paths P1, P2 to form an output voltage across a resistor 126.

The drawing of FIG. 2 depicts a basic SAW interferometer; however, a wide variety of improvements can be made to optimize the design and improve the performance of the SAW transducer structures as is well known in the art. One refinement of the basic structure is the use of unidirectional SAW transducers for the input transducers 110′, 112′. The interdigital structures shown in FIG. 2 are bidirectional; however, techniques have been developed based on concepts of quadrature phase addition that enable SAW transducers to radiate and receive energy in only one direction. The use of a unidirectional SAW transducer for the input transducers 110′, 112′ would improve the performance of the illustrated design since it would lower the loss of the device and reduce the amount of energy transferred into undesired beam components.

FIGS. 3–9 show simple schematic views of a number of ways the acoustic wave interferometers 100, 102 can be used to sense a variety of physical phenomena. FIG. 3 schematically shows a SHAW interferometer used as an accelerometer 132. Masses 134 are attached to both ends of the plate 104. When the plate accelerates to the right as shown in FIG. 3, because of the inertia of the masses 134, the path P1 on the left side of the plate 104 will be lengthened and the path P2 on the right side of the plate 104 will be shortened. If the accelerometer 132 is adjusted for a null in the output signal when it is at rest, the relative phase shift produced by the changes in the two paths P1, P2, will produce an output signal proportional to the acceleration.

In the application of FIG. 3, both paths P1, P2 of the interferometer of the accelerometer 132 change in length and work together. As will become apparent, in many applications, only one path changes in response to a physical phenomenon to be sensed and the other path remains substantially constant or changes significantly less than the one path.

The accelerometer 132 of FIG. 3 can also be modified and used as a yaw rate sensor 136 as shown in FIG. 4. The modification is performed by attaching support structure that places the accelerometer 132 off an axis 138 of rotation and that rotates the accelerometer 132 about the axis 138. The signal generated by the accelerometer 132 will be proportional to the angular velocity of the sensor 136.

FIG. 5 shows a SAW interferometer used as an accelerometer 140. Because the wave motion is concentrated near the upper surface of the silicon plate 104, it is possible to take advantage of the greater compliance of a thin plate in flexure. One end 104E of the plate 104 is secured to a support structure 142 and the other end 104F has a mass 144 attached to it. An acceleration in the vertical direction will cause the plate 104 to flex, lengthening the path P2 in the right side of the plate 104 when the plate 104 bends down and decreasing the path P2 when the plate 104 bends up. Alternately, the mass 144 can be replaced by a contact 146 that applies a force to the unsupported end 104F of the plate 104 of the SAW interferometer, as shown in dotted lines.

FIG. 6 illustrates how an acoustic interferometer can be used as a chemical composition sensor 147, used, for example, to sense the concentration of one or more gases. The region including the path P2 along which the beam travels on the right side of the plate 104 is coated with a substance 148 that preferentially absorbs the chemical composition to be sensed. Depending upon the particular chemical composition, the absorbed chemical species may be a whole class of gases like hydrocarbons or a single gas like carbon monoxide.

When the gas is adsorbed, the mass loading of the surface area coated with the substance 148 increases and the phase velocity of the wave motion is decreased. The phase length of the path P2 is thus increased producing a signal at the output of the acoustic interferometer. If the substance 148 coating the path P2 of FIG. 6 absorbs moisture, then the arrangement of FIG. 6 can also be used as a humidity sensor.

Figure 9:
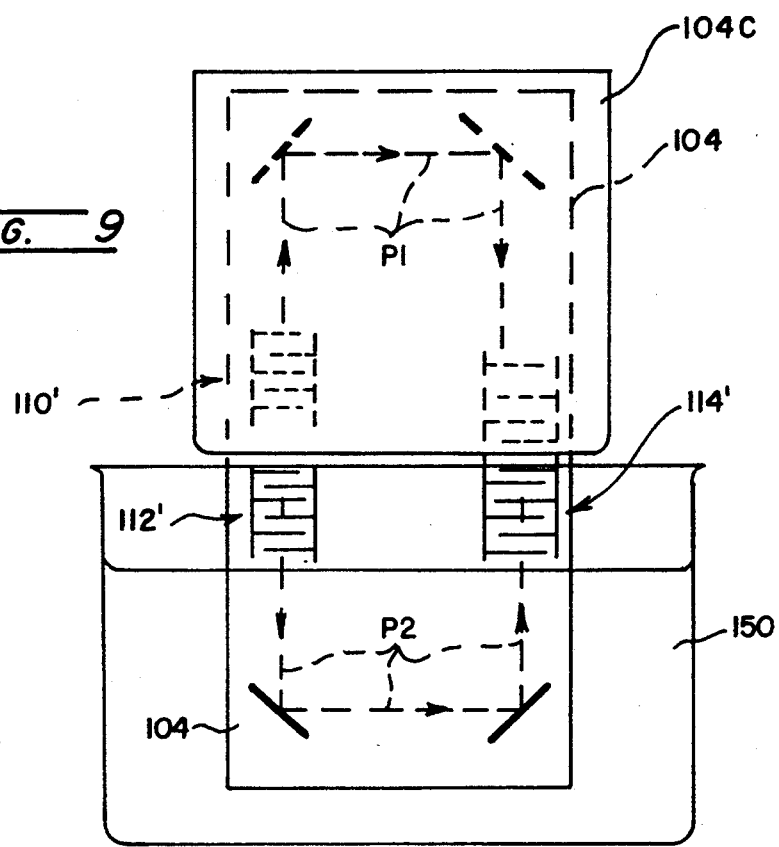

FIG. 9 shows how an acoustic interferometer may be used as a viscosity sensor for a viscous liquid 150. Half of the plate 104 is immersed into the liquid 150 while the other half is covered by a protective coating 104C to permit handling without substantially effecting the transmission characteristics of the path P1. The liquid 150 places a mechanical loading on the surface immersed therein to influence both the attenuation and the phase velocity of acoustic waves passing along the path P2.

If the density changes are relatively slight, changes in viscosity will produce primarily changes in attenuation of the acoustic wave motion in the immersed path P2 of the interferometer. The change in attenuation will produce an imbalance at the output of the interferometer and permit the viscosity change to be sensed thereby.

Figure 8:
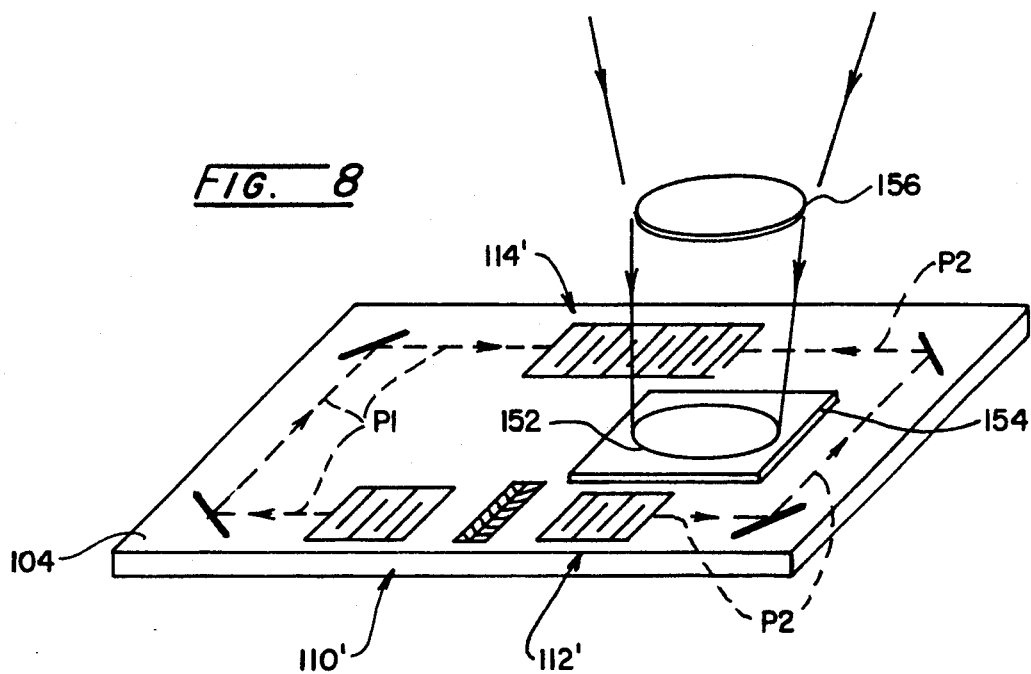

FIG. 8 illustrates another application for an acoustic interferometer as a sensor for electromagnetic radiation such as infrared radiation. In the application of FIG. 8, the right side of the device which includes the path P2 has a cavity 152 formed therein. The cavity 152 is filled with a fluid medium that absorbs energy incident in the wavelength range of interest, for example infrared. The fluid medium is sealed in the cavity 152 with a thin, transparent, cover plate 154. Appropriate optical coupling apparatus, indicated in FIG. 8 by a lens 156, directs and concentrates the electromagnetic energy to be sensed on the sealed cavity 152. For infrared sensing, as thermal energy is absorbed, the fluid in the cavity 152 expands and stresses the silicon in the walls of the cavity 152, causing the length of the path P2 surrounding the cavity 152 to increase and thereby produce a corresponding output signal.

FIG. 7 illustrates use of an acoustic interferometer as a magnetic field sensor 157. While only the upper surface of the silicon plate 104 is shown in FIG. 7, both the upper and lower surfaces adjacent to the path P2 along the right side of the plate 104 are plated, or otherwise have deposited thereon, films 158 of a magnetic material such as nickel. Since magnetic films are magnetostrictive, the films 158 are deposited to avoid areas corresponding to the beam path P2 and do not extend into the areas of the plate 104 occupied by the transducers 110′, 112′, 114′.

A magnetic field 160 present in the space of the sensor, for example due to current flow through a wire 162 placed in close proximity to the sensor 157, will cause the right side of the plate 104 to experience strain which will change the total phase length of the path P2 along the right half of the plate 104. For some applications, like sensing whether or not a conductor is carrying a current, it may be desirable to form a magnetic circuit consisting of a thin ribbon of magnetic (high permeability) material that brings the magnetic field from its region of origin and concentrates the magnetic field over the sensitive side of the interferometer.

It may be preferred in some applications to form the magnetic material deposited on one or both sides of the plate 104 into a number of parallel, thin, rectangular strips 164. Such patterns of strips would make the sensor 157 have a directional sensitivity, having a maximum response when the strips 164 are aligned in the same direction as the magnetic field to be sensed. The structure of such a device is substantially the same as that shown in FIG. 7 except that the film 158 is plated in long thin parallel stripes. The stripe length can be either in the width direction of the plate 104, as shown, or in the length direction of the plate 104. An opening 166 can be formed through the portion of the plate 104 including the path P2 and the conductor 162 can be passed through the opening 166. The strip length as shown in FIG. 7 would generally correspond to having the conductor 162 passed through the opening 166 such that the field generated by current flow through the conductor 162 is generally parallel to the strips 164.

Having thus described the invention of the present application in detail and by reference to preferred embodiments thereof, it will be apparent that modifications and variations are possible without departing from the scope of the invention defined in the appended claims. For example, numerous additional sensors utilizing acoustic or ultrasonic interferometry will be suggested to those skilled in the art in view of the foregoing illustrations and description.

What is claimed is:

1. An ultrasonic wave interferometer device comprising:
   a section of ultrasonic wave transmission media for defining substantially isolated coplanar first and second ultrasonic wave paths therethrough, said first and second ultrasonic wave paths each having an input end and an output end and defining substantially equal transmission characteristics from said input ends to said output ends for a neutral condition of said device;
   ultrasonic wave transmitters coupled to said media for introducing ultrasonic waves into said input ends of said first and second ultrasonic wave paths;
   an ultrasonic wave receiver coupled to said media for receiving and combining ultrasonic waves from said output ends of said first and second ultrasonic wave paths and for generating an output signal representative of the combination of ultrasonic waves from said first and second ultrasonic wave paths as said ultrasonic waves are received from said output ends of said first and second ultrasonic wave paths;
   a drive circuit for driving said ultrasonic wave transmitters to generate ultrasonic waves in said first and second ultrasonic wave paths; and
   a receiver circuit for receiving said output signal generated by said ultrasonic wave receiver.

2. An ultrasonic wave interferometer device as claimed in claim 1 wherein said drive circuit comprises an oscillator and drive adjuster circuit for effectively equalizing drive signals provided to said ultrasonic wave transmitters for nulling said output signal generated by said ultrasonic wave receiver when said device is in said neutral condition.

3. An ultrasonic wave interferometer device as claimed in claim 1 further comprising a monitor circuit for monitoring said receiver circuit for determining whether said neutral condition of said device is maintained.

4. An ultrasonic wave interferometer device as claimed in claim 3 wherein at least one of said first and second ultrasonic wave paths comprises path altering means coupled thereto for changing the transmission characteristics of at least one of said first and second ultrasonic wave paths as the result of a physical phenomenon whereby said physical phenomenon can be sensed by alteration of said neutral condition of said device.

5. An ultrasonic wave interferometer device as claimed in claim 4 wherein said section of ultrasonic wave transmission media comprises a plate-like member with said coplanar first and second ultrasonic wave paths being formed in substantially isolated portions of said plate-like member, and said path altering means is coupled to at least one of said substantially isolated portions.

6. An ultrasonic wave interferometer device as claimed in claim 5 wherein said plate-like member comprises a generally rectangular solid plate formed from single-crystal silicon.

7. An ultrasonic wave interferometer device as claimed in claim 5 wherein said path altering means comprises a first mass coupled to change said first ultrasonic wave path upon acceleration of said device.

8. An ultrasonic wave interferometer device as claimed in claim 7 wherein said path altering means comprises a second mass coupled to change said second ultrasonic wave path upon acceleration of said device.

9. An ultrasonic wave interferometer device as claimed in claim 4 wherein said path altering means comprises sensor means associated with one of said first and second ultrasonic wave paths for sensing a given physical phenomenon and altering said one of said first and second ultrasonic wave paths as the result of sensing said given physical phenomenon.

10. An ultrasonic wave interferometer device as claimed in claim 9 wherein said sensor means comprises magnetic material associated with said one of said first and second ultrasonic wave paths for sensing a magnetic field imposed upon said one of said first and second ultrasonic wave paths.

11. An ultrasonic wave interferometer device as claimed in claim 9 wherein said sensor means comprises an infrared radiation sensor associated with said one of said first and second ultrasonic wave paths for sensing infrared radiation incident upon said one of said first and second ultrasonic wave paths.

12. An ultrasonic wave interferometer device as claimed in claim 9 wherein said sensor means comprises a chemically sensitive coating associated with said one of said first and second ultrasonic wave paths for sensing the presence of a chemical upon said one of said first and second ultrasonic wave paths.

13. An ultrasonic wave interferometer device for performing ultrasonic wave interferometry comprising:
   coplanar first and second substantially isolated ultrasonic transmission paths defining substantially equal transmission characteristics when said device is in a neutral condition;
   a first transducer coupled to said first ultrasonic transmission path for launching ultrasonic waves in said first ultrasonic transmission path;
   a second transducer coupled to said second ultrasonic transmission path for launching ultrasonic waves in said second ultrasonic transmission path, said ultrasonic waves launched in said second ultrasonic transmission path being effectively identical to said ultrasonic waves launched in said first ultrasonic transmission path;
   a third transducer coupled to said first and second ultrasonic transmission paths for receiving and combining ultrasonic waves transmitted through said first and second ultrasonic transmission paths, said third transducer generating an output signal representative of the combination of the ultrasonic waves received from said first and second ultrasonic transmission paths; and coupler means for coupling a physical phenomenon to at least one of said first and second ultrasonic transmission paths whereby said physical phenomenon can be detected.

14. An ultrasonic wave interferometer device for performing ultrasonic wave interferometry as claimed in claim 13 wherein said coplanar first and second ultrasonic transmission paths are defined in a generally rectangular solid plate formed from single-crystal silicon.

15. An ultrasonic wave interferometer device for performing ultrasonic wave interferometry as claimed in claim 14 wherein said coupler means comprises at least two strips of magnetic material associated with one of said first and second ultrasonic transmission paths for sensing a magnetic field upon said one of said ultrasonic transmission paths, said at least two strips being aligned with said magnetic field.

16. An ultrasonic wave interferometer device for performing ultrasonic wave interferometry as claimed in claim 14 wherein said coupler means comprises magnetic material associated with one of said first and second ultrasonic transmission paths for sensing a magnetic field upon said one of said ultrasonic transmission paths.

17. An ultrasonic wave interferometer device for performing ultrasonic wave interferometry as claimed in claim 15 wherein said coupler means further comprises an opening through said ultrasonic wave device and associated with said one of said first and second ultrasonic transmission paths for receiving an electrical conductor therethrough whereby current flow in said electrical conductor can be sensed by sensing the magnetic field generated about said electrical conductor due to said current flow.

18. A method of sensing physical phenomena by means of ultrasonic energy interferometry comprising the steps of:

defining substantially isolated coplanar first and second ultrasonic energy paths having substantially equal transmission characteristics when said first and second ultrasonic energy paths are in a neutral condition;

coupling a physical phenomenon to at least one of said first and second ultrasonic energy paths;

passing substantially identical ultrasonic energy waves through said first and second ultrasonic energy paths;

receiving and combining ultrasonic energy transmitted through said first and second ultrasonic energy paths; and generating a signal indicative of the combination of ultrasonic energy received after transmission through said first and second ultrasonic energy paths, said signal being representative of said physical phenomenon.

19. A method of sensing physical phenomena by means of ultrasonic energy interferometry as claimed in claim 18 further comprising the step of nulling said signal when said first and second ultrasonic energy paths are in said neutral state.

20. A method of sensing physical phenomena by means of ultrasonic energy interferometry as claimed in claim 19 further comprising the step of maintaining a record of said signal.

21. An ultrasonic wave interferometer device for performing ultrasonic wave interferometry comprising:

coplanar first and second substantially isolated ultrasonic transmission paths, said first and second ultrasonic transmission paths differing in length by one-quarter wavelength from one another when said device is in a neutral condition;

a first transducer coupled to said first ultrasonic transmission path for launching ultrasonic waves in said first ultrasonic transmission path;

a second transducer coupled to said second ultrasonic transmission path for launching ultrasonic waves in said second ultrasonic transmission path, said ultrasonic waves launched in said second ultrasonic transmission path being effectively identical to said ultrasonic waves launched in said first ultrasonic transmission path;

a third transducer coupled to said first and second ultrasonic transmission paths for receiving and combining ultrasonic waves transmitted through said first and second ultrasonic transmission paths, said third transducer generating an output signal representative of the combination of the ultrasonic waves received from said first and second ultrasonic transmission paths; and coupler means for coupling a physical phenomenon to at least one of said first and second ultrasonic transmission paths whereby said physical phenomenon can be detected.

* * * * *